United States Patent [19]

Grim

[11] 4,092,544
[45] May 30, 1978

[54] X-RAY PHOTOGRAPHIC APPARATUS COMPRISING LIGHT SOURCE AND RECEIVING DEVICE ARRANGED TO FACILITATE THE ALIGNMENT OF THE APPARATUS

[75] Inventor: Stig Grim, Osterskar, Sweden

[73] Assignee: Siemens Aktiengesellschaft, Berlin & Munich, Germany

[21] Appl. No.: 767,538

[22] Filed: Feb. 10, 1977

[30] Foreign Application Priority Data

Mar. 1, 1976 Germany .............................. 2608452

[51] Int. Cl.² .............................................. A61B 6/08
[52] U.S. Cl. ..................................... 250/491; 250/511
[58] Field of Search ............... 250/511, 320, 480, 481, 250/491

[56] References Cited

U.S. PATENT DOCUMENTS

| | | | |
|---|---|---|---|
| 1,794,853 | 3/1931 | Herrnheiser | 250/491 |
| 1,976,179 | 10/1934 | Mannl | 250/491 |
| 3,764,808 | 10/1973 | Lackey et al. | 250/511 |
| 3,857,039 | 12/1974 | Franke et al. | 250/511 |
| 3,920,997 | 11/1975 | Munch | 250/511 |
| 4,048,507 | 9/1977 | Gaston | 250/491 |

Primary Examiner—Alfred E. Smith
Assistant Examiner—T. N. Grigsby
Attorney, Agent, or Firm—Hill, Gross, Simpson, Van Santen, Steadman, Chiara & Simpson

[57] ABSTRACT

This invention discloses an X-ray photography device having an X-ray tube associated with a primary diaphragm for defining or limiting the X-ray beam by partially blocking the same. The X-ray tube is mounted or carried in such a fashion that the beam can be directed at random towards any desired target. The device further includes a film cassette constituting a desired target which is similarly freely movable at random independently of the X-ray tube. Means are provided to accurately align the X-ray beam and target and to insure proper target coverage by the beam.

19 Claims, 7 Drawing Figures

X-RAY PHOTOGRAPHIC APPARATUS COMPRISING LIGHT SOURCE AND RECEIVING DEVICE ARRANGED TO FACILITATE THE ALIGNMENT OF THE APPARATUS

BACKGROUND OF THE INVENTION

1. Field of the Invention

This invention relates to X-ray photographic devices.

2. Prior Art

X-ray photographic apparatus of the non-integrated type where the X-ray tube module is substantially independent from the target module are known to the art. In diagnostic radiology apparatus of this type is often employed for producing X-ray photographs of bedridden patients. In such instances, when the patient cannot be taken to a large fixed bed X-ray machine, mobile mounted X-ray apparatus are brought to the patient. Independent film cassettes are arranged beneath or next to the patient and the X-ray beam is directed at the target cassette. Such devices normally include a wheel mounted member equipped with articulated supports or arms to which the X-ray tube is secured. The tube may therefore be simply adjusted to any desired position such that the beam will be directed relative to the patient and the film cassette.

In the case of medical X-ray image photographs, it is desirable to produce both the best possible image sharpness and contrast while exposing the patient to the least possible radiation dosage. It is also desirable to limit the dosage for protection of the personnel conducting the examination.

In practice, in order to achieve the desired image result, the beam is restricted by a diaphragm associated with the X-ray tube housing. This restriction of the diaphragm aperture is of major significance. Among other things, the X-ray photograph image impairing effect produced by secondary radiation emitting from the patient and which results in background veiling or ghost imaging is reduced by diaphragm limitation. However proper adjustment of the diaphragm is difficult to realize in those instances where a mechanical linkage or coupling between the X-ray tube and the film cassette is not present. The obvious and most often practiced process is to align the X-ray beam in relation to the film cassette by eyeballing the relative disposition of the X-ray tube housing, the primary diaphragm and the film cassette. A major disadvantage with such eyeballing is that if the X-ray beam is too narrowly limited by the diaphragm, the desired image is only partially obtained. In order to avoid this it is common practice to leave the diaphragm setting wider than is necessary for use in connection with the particular cassette employed, thereby resulting in an unnecessar large radiation dose.

Additionally, good stopping-down of the X-ray beam by the diaphragm is of major significance in the reduction of the charge or burden of the overall radiation dose on the patient. As a result, the appropriate government agency in the United States has required automatic diaphragm limitation of the X-ray beam to the format of the film or cassette. Yet due to technical difficulties involved, an exception to this requirement is made for devices of the type in which a mechanical coupling or linkage between the X-ray tube and the film cassette does not exist. Thus, an exception from the automatic diaphragm rule specifically applies to the apparatus of the type above described. However, it would obviously be desirable to provide for such precise limiting of the beam in such apparatus.

A number of attempts have been made to limit undesired radiation. One such method of making secondary radiation less disruptive of image clarity is through the use of a so-called secondary radiation or raster screen. Raster screens may be composed of lead laminae standing on edge and having a high degree of X-ray absorption. The lead laminae are surrounded by a medium with relatively low absorption. Such raster screens are arranged between the patient and the film cassette. To the extent that the surface of the raster screen is not at right angles in relation to the central ray of the X-ray beam, the image producing direct radiation will be absorbed by the laminae in addition to the laminae's absorption of the secondary radiation. This results in a so called raster effect. The raster effect is very bothersome in practice, and often, particularly in the case of bedridden patients, leads to repeated X-ray photographs having the consequence of both an increased radiation dose on the patient and an increased consumption of film.

British patent 861,550 teaches an X-ray device having an examination table providing support for the patient. The table is used in connection with apparatus mechanically coupling the X-ray tube with the table in such a manner that only limited movement of the X-ray tube may be carried out in relation to the support or patient bearing surface. A light beam aligned with the central ray of the X-ray beam is used to mark the position or orientation of the central ray in relation to the patient and in relation to a movable cassette holder or container lying beneath the support surface. The light beam is produced by one or more light sources which are mechanically coupled to the X-ray tube. This apparatus, which requires a mechanical coupling between the X-ray tube and the film cassette, allows a visual showing of the relative position of the X-ray tube and the film cassette, but only for limited allowable movements of the X-ray tube and cassette. The apparatus taught by this patent cannot be used in association with X-ray photographic apparatus of the above discussed or non-integrated type.

It would therefore be an advance in the art to provide an X-ray apparatus having independently movable X-ray beam generating apparatus and film cassette apparatus but which provides a means for precisely aligning the X-ray beam with the cassette and for properly limiting the beam spread.

SUMMARY OF THE INVENTION

It is therefore a primary object of this invention to create an X-ray photographic apparatus of the non-integrated type above described wherein the film cassette, or the X-ray tube, or both, can be simply and rapidly adjusted to the optimum relative positions.

This object is solved in accordance with the teachings of this invention by providing a light source which is spatially positioned in fixed association with the primary diaphragm and/or the X-ray tube. The light source is provided with means for geometrically defining or limiting the light beam and is used in association with a cassette which has a target marking thereon or on an element rigidly connected to the cassette. The target marking is constructed such that impingement of the light beam from the light source on the target marking will result in a recognizable indication as to whether the edges of the cassette are properly parallelly aligned to the edges or peripheries of the X-ray beam. Also indicated is whether the central ray of the X-ray beam is aligned perpendicularly to the center of the cassette. It is also desired to further indicate whether the correct focus-to-film spacing or distance exists. In the embodiments shown the light source is arranged such that the light beam is not interrupted or blocked by the patient.

The optimum position for the combination of the X-ray tube, the diaphragm and the cassette has the following radiation-geometric relationship requirements. First, the central ray of the X-ray beam should strike the central point of the film cassette. Second, when utilizing a primary diaphragm of the type which yields a quadralateral or square radiation field, the boundary surfaces or peripheries of the beam should lie parallel to the edges of the film cassette. Third, the distance between the focus of the X-ray tube and the position of the film cassette, i.e. the focus-to-film distance, should correspond to a predetermined value. Fourth, the central ray of the X-ray beam should strike the surface of the film cassette at a substantially right angle.

In a specifically designed embodiment of the invention, an adjusting device for adjusting the focusing system for the light beam delivers a signal which is dependent upon the particular focus-to-film distance to which the focusing system is adjusted. The signal for the focus-to-film distance and an additional signal dependent upon the size of the cassette are fed to a computing circuit which, by means of servomotors, controls the primary diaphragm to assure that the X-ray beam is so defined or limited such that its boundaries surfaces or peripheries will, in the plane of the film cassette, coincide with the edges of the film cassette. This is true even in the event of different focus-to-film distances. Thus, this invention provides a device wherein the X-ray beam is automatically correctly adjusted in relation to the film cassette in spite of the fact that both the X-ray tube and the film cassette are independently movable and are not mechanically coupled together and further, in spite of the fact that different focus to film distances may be utilized.

Objects, features and advantages of the invention will be readily apparent from the following description of a preferred embodiment thereof, taken in conjunction with the accompanying drawings, although variations and modifications may be effected without departing from the spirit and scope of the novel concepts of the disclosure, and in which:

DESCRIPTION OF THE PREFERRED EMBODIMENTS

Figure 1:
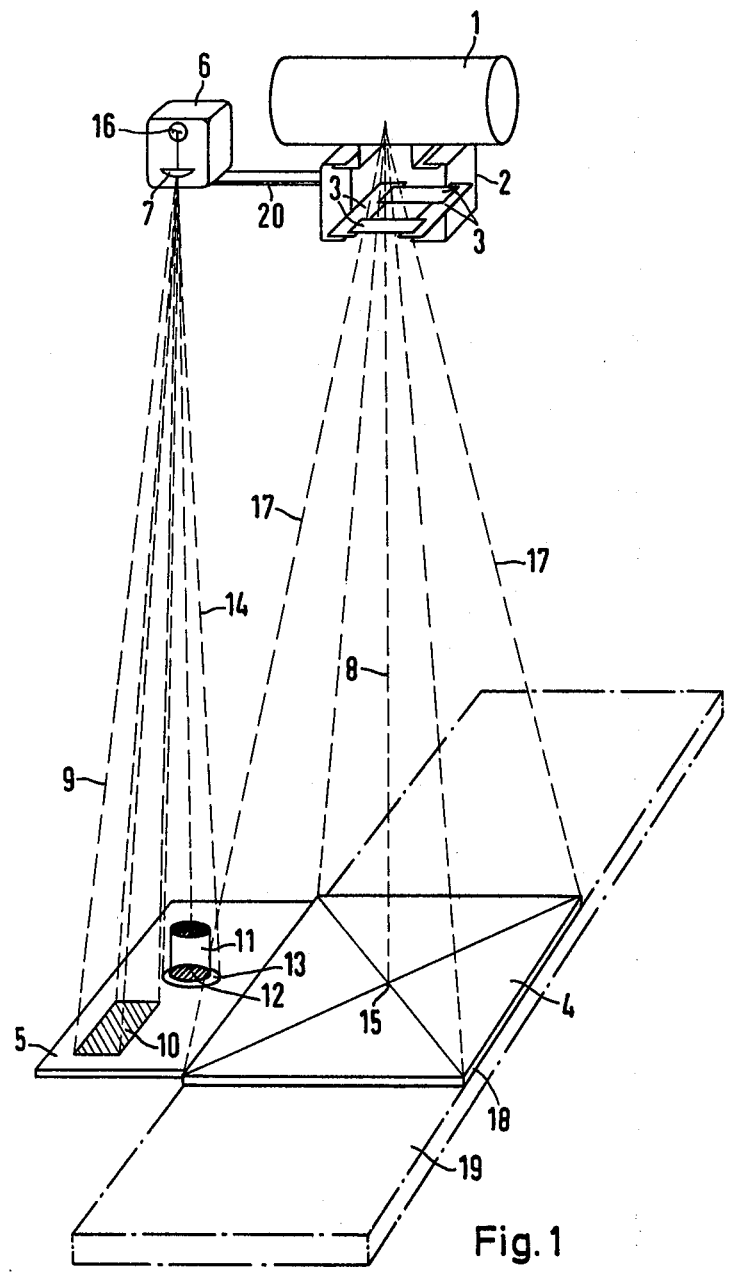
FIG. 1 is a diagrammatic descriptive drawing of an X-ray device according to this invention.

FIG. 1 illustrates an X-ray photographic apparatus according to this invention. The device is provided with an X-ray tube 1 which is, as is known to those skilled in the art, supported either from the ceiling or on a movable floor stand (not shown). Additionally, the apparatus includes a film cassette which is insertable, for example, between an examination table 19 and a patient received on the table. A primary diaphragm 2 associated with the X-ray tube 1 is equipped with two pairs of laminae 3 which are capable of blocking the radiation from the tube 1. The pairs of laminae have the laminae in each pair movable towards and away from one another and the pairs are movable with respect to the other pair at right angles thereto. Thus it is possible to stop down or reduce the aperture defined between the pairs to limit the X-ray beam eminating from the diaphragm 2. Additionally this type of diaphragm provides a quadralateral beam. Preferably, and particularly for photographs involving bedridden patients with mobile X-ray apparatus, the primary diaphragm is arranged to be rotatable in relation to the X-ray tube 1 about an axis coinciding with the axis of the central ray 8 of the X-ray beam. The X-ray tube 1 and the primary diaphragm 2 are, via a projecting arm 20, fixedly and rigidly connected to a light source 16 contained in a housing 6. The housing includes a lens system 7 defining or limiting the light beam from the light source 16 and directing it in the same direction as the X-ray beam 17.

An extension or projection 5 rigidly connected to the cassette 4 is provided with a mark providing a defined field 10. The mark 10 is provided for the purposes of determining the position of the edges 18 of the cassette in relation to the boundary lines or peripheries of the X-ray beam striking the cassette. The mark also is provided for the purpose of determining the film to focus distance. Additionally a shadow producing arrangement 11 is provided for the purpose of determing the angle between the central ray 8 and the surface of the cassette 4.

Prior to taking an X-ray photograph, the tube 1 and film cassette 4 are brought into relative position to the point that the edges of the light beam 9 from light source 16 strike the mark 10 in a specified manner. If the X-ray tube 1 is a predetermined distance from the cassette 4, the lines defining the edges of the light beam which are visible on the extension 5 will coincide with the field of the mark 10. When this is the case, or when the lines are positioned symmetrically to the mark field 10, the central ray 8 of the X-ray beam will be aligned with the center 15 of the film cassette 4. This then also means that the peripheral edges of the quadralateral X-ray beam 17 will be positioned parallel to the edges 18 of the cassette 4. Thereafter by means of the blocking laminae 3 of the primary diaphragm it is possible to align the peripheries of the X-ray beam 17 with the peripheries 18 of the film cassette.

Therefore, as can be seen from the above, the marking 10 in combination with the light beam 9 will permit a relative alignment of the X-ray tube 1 and the cassette which assures that the edges of the cassette lie parallel to the cross-sectional boundaries of the X-ray beam striking the cassette or that they coincide with the beam edges. The necessary alignment can be carried out by moving or adjusting the X-ray tube 1 in relation to the cassette 4. Further, by means of a size comparison between the size of the light beam field projected on the section 5 with the size of the marking 10, the focus to film distance can be determined.

As further shown in FIG. 1, a shadow producing assembly 11 is mounted perpendicularly on the extension 5 of the film cassette and includes an upper surface which is opaque to light. The assembly 11 may be composed of a synthetic glass or plastic cylinder having a blackened axial end. The shadow producing assembly 11 is illuminated by means of a second light beam 14 produced by the light source 16 via the lens system 7. This second light beam 14 strikes the center of the assembly 11 when the cross-sectional boundary or marginal edge lines of the light beam 9 coincide with the edges of field 10 or are disposed symmetrically and parallel thereto. Further the second light beam 14 is preferably parallel to the central ray 8 of the X-ray beam 17. Thus, the shadow 12 of the opaque surface of assembly 11 cooperates with a marking or pattern 13 on the projection 5. In this manner the X-ray tube 1 and cassette 4 can be brought into such a relative position that the central ray 8 is perpendicular to the surfaces of the cassette.

The light beam 9 is limited, defined or spotted and may, if desired, be divided into two or more light beams each of which is limited or sharply defined in certain directions which correspond to two or more defined marked fields. However, it is a central feature of this invention that the boundary lines of the light beam or light beams be projected on the extension or section 5 of the cassette in such a way as to permit the illustrated alignment and distance determinations of the mark.

Additionally, the field or marking 10 may be supplemented by additional fields or markings in order to allow determination of different focus-to-film distances by proper illumination thereof by the light beam or beams 9.

Figure 2:
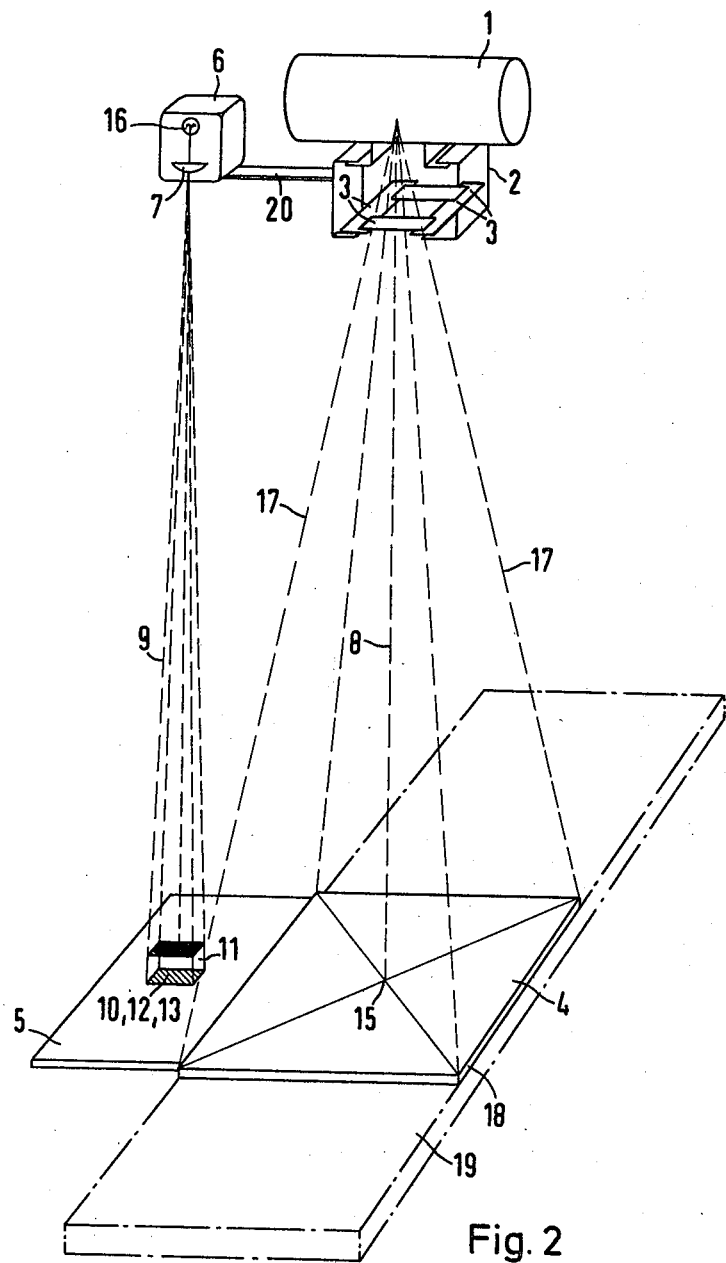
FIG. 2 is a view similar to FIG. 1 illustrating in modification of the device of FIG. 1.

FIG. 2 illustrates a variation of the device of FIG. 1 wherein the marking or field 10 coincides with the marking or pattern 13 and therefore with the shadow 12 of the shadow producing assembly 11. In this instance, the shadow producing assembly may be composed of a clear or light permeable cube having a top surface coated with a light absorptive or opaque color.

Figure 3:
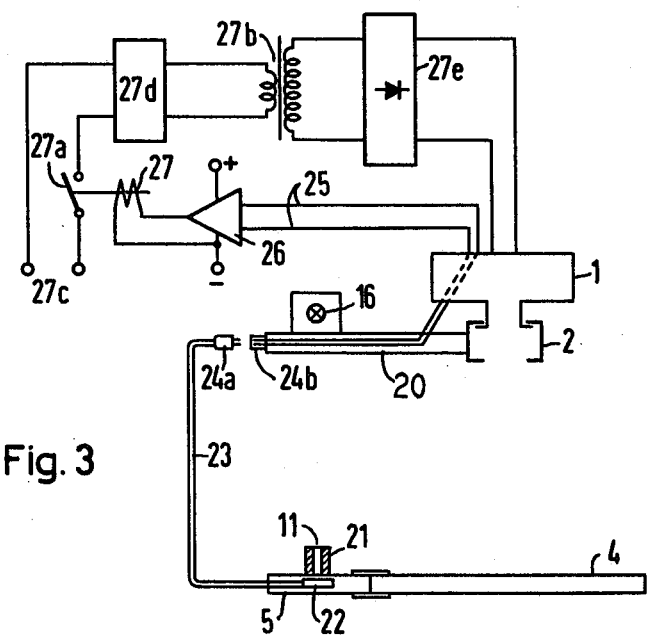
FIG. 3 is a circuit diagram disclosing a circuit arrangement for controlling the diaphragm of the X-ray tube.

FIG. 3 illustrates yet another shadow producing assembly which is coupled to the main circuitry for the X-ray tube 1 to limit actuation to those periods when the beam from the X-ray tube is properly aligned with a cassette. In this embodiment the shadow producing assembly 11 may include a tube or hollow cylinder projecting upwardly from the extension 5 to the cassette 4. The walls of the tube are opaque light absorptive and a light beam will be transmitted axially of the tube from the top to the bottom only when the light beam is substantially parallel to the axis of the tube. Either the extension 5 to the cassette or the tube 11 and be equipped, at the bottom end of the tube, with a light sensing device such as a photoelectric sensor 22. The light sensing device acts, in a known manner to deliver a signal which can be used to allow activation of the X-ray tube 1 only when the light passing from a light source through the tube 21 reaches the sensor 22 thereby indicating correct positioning of the X-ray tube with respect to the cassette 4 such that the central ray of the X-ray tube is at a right angle relationship with the cassette 4.

As further shown in FIG. 3, a line connection 23 to the sensor 22 may terminate in a plug 24a which is insertable in a plug socket 24b positioned at the end of the arm 20. Line 23, when plugged in, connects with line 25 to an amplifier or intensifier 26. This cooperates such that when light strikes the sensor 22 relay 27 will be activated completing a main power circuit to high voltage transformer 27b. One of the main supply terminals is illustrated at 27c.

The main circuit may include a switching device 27d connected to the main supply which may, for example, constitute an exposure time control in a known manner. In addition, high voltage rectifier 27e may also be provided.

Figure 4:
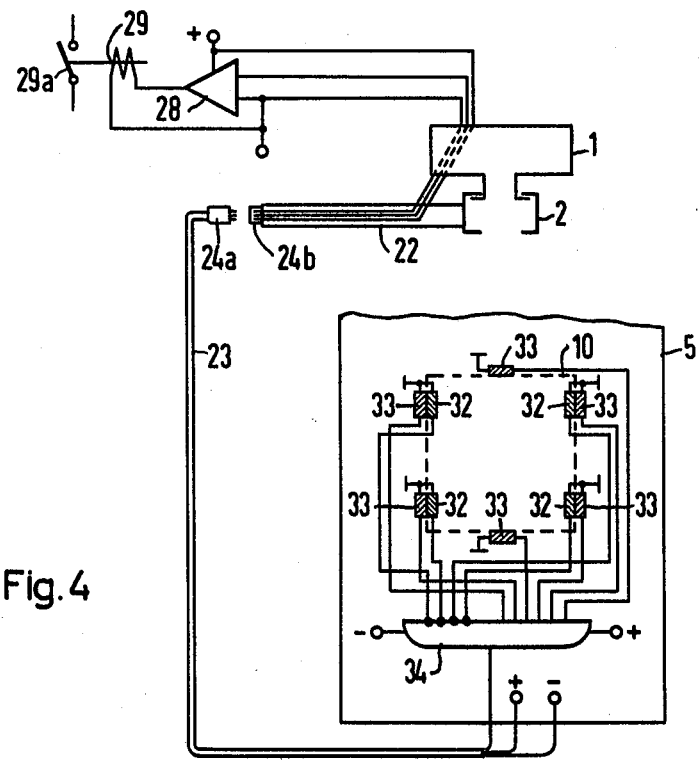
FIG. 4 is a second circuit diagram illustrating a diaphragm control circuit.

As illustrated in FIG. 4, a second automatic light recognizing assembly 32, 33, 34 may be utilized in connection with the marking 10. In this instance the second assembly can be designed to deliver a signal when the margins or edges of the light beam 9 impinge upon the area of the marking 10 in a predetermined, desired manner, the signal being used to prevent an X-ray photograph from being taken if the signal is absent. The position of the cassette as used in relation to the X-ray beam can therefore be determined by a structure such as shown in FIG. 4.

In FIG. 4, 32 and 33 represent photoelectric cells which record the intensity of the impinging light received thereat. In the circuit illustrated, if the light strikes the 4 photoelectric cells 32 but does not strike the 6 photoelectric cells 33, an electric signal will be delivered from the AND gat 34 and will be conveyed through lines 23 and the plug connection 24a, 24b to an amplifier 28. The amplifier will cause actuation of a relay 29 to release a previous blockage of the trigger or actuation circuit for the X-ray tube 1. This trigger circuit may be substantially similar to the contact 27a illustrated in FIG. 3.

Figure 5:
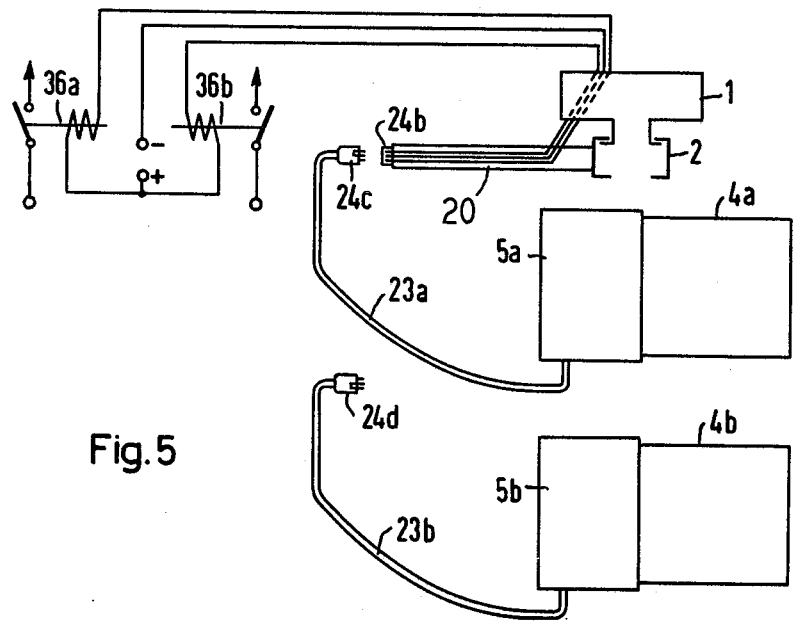
FIG. 5 is a circuit diagram for producing a signal dependent upon the size of the film cassette being used in the apparatus.

In those instances where different forms or shapes of cassettes are to be used in association with the same X-ray tube 1, means may be provided to deliver a signal dependent upon size of the cassette. For example, in FIG. 5, two cassettes 4a and 4b of different sizes are illustrated. Cable 23a or 23b is associated with each of the extensions 5a and 5b which are equipped with the markings or measuring apparatus according to FIGS. 1 and 2. For simplicity, the cables may not be equipped with any additional lines for cassette identification but they instead may be provided with plugs 24c or 24d which can be plugged into the matching counter plug 24b. By short circuiting different pins in the plugs 24c and 24d, the plugs can be used, when inserted, to activate a preselected relay 36a or 36b to close its associated contact thereby delivering a signal used by the system to indicate the size of the cassette being utilized.

Figure 6:
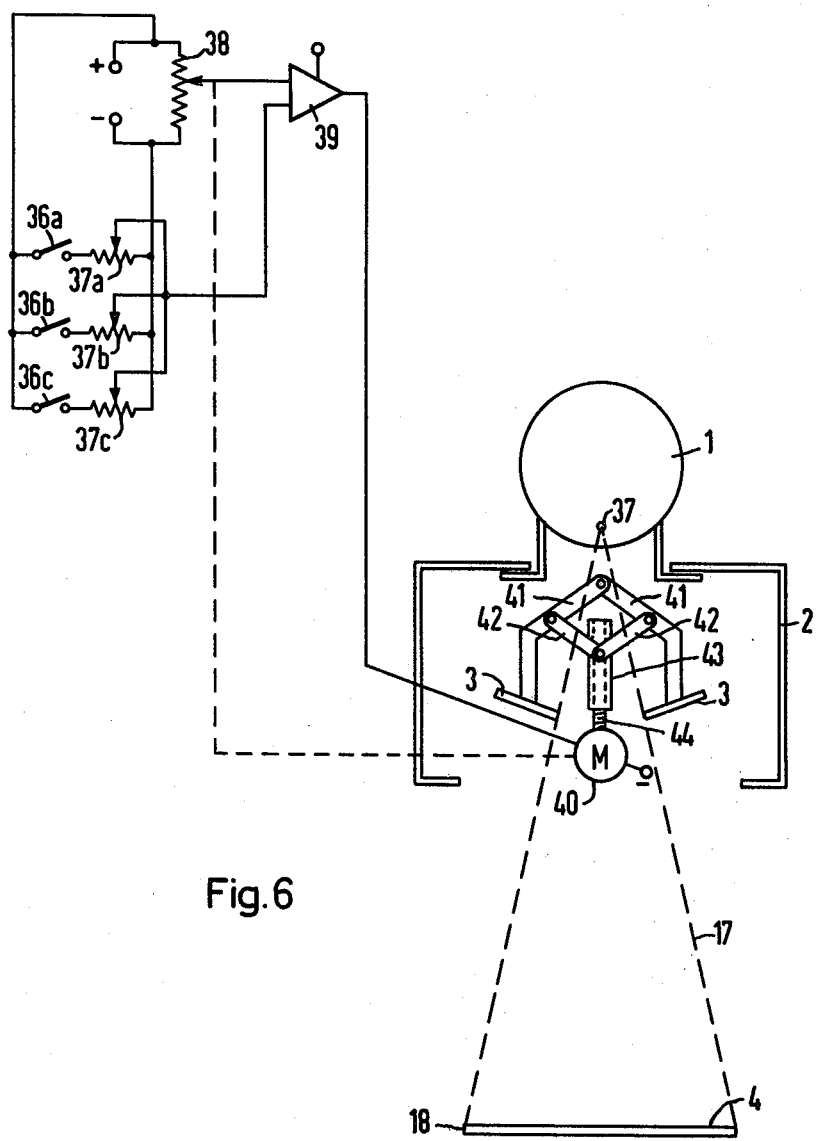
FIG. 6 is a control circuit and mechanism illustrating a diaphragm adjustment system.

Additionally, as is shown in FIG. 6, the diaphragm can be automatically controlled. When the focus 37 of the X-ray tube 1 is at a specific distance from the film cassette 4, thereby closing the contact described in FIG. 4, and when the central ray 8 of the X-ray beam impinges upon the cassette 4 in the center of the cassette at a right angle, thereby closing the relay contact 27a as shown in FIG. 3, servomotors 40 may be used to properly adjust the diaphragm 2 in dependence to a signal which characterizes the cassette size or format. The motors 40 can be used to automatically cause the diaphragm 2 to limit the X-ray beam 17 in such a manner that is boundary lines or margins, in the plane of a known sized film cassette 4 will coincide with the edges 18 of the cassette.

FIG. 6 illustrates a single motor 40 for controlling two laminae 3 of the diaphragm 2 in an automatic control circuit including relays 36a, 36b and 36c, 37a and potentiometers 37b, 37c and 38 and coparator 39. The motor 40 moves the laminae 3, for example, by means of a rotating screw 44 received in a movable bushing 43 which acts through linkage 41 and 42 to cause movement of the laminae 3 towards and away from one another. The motor 40 is mechanically connected with the arm of a potentiometer 38 whose output voltage corresponds to the value of the position of the laminae 3. The actual value is compared with a desired value in a differential amplifier 39, the desired value being inputed to the differential amplifier from the voltage of one of the potentiometers 37a, 37b or 37c, that voltage being dependent upon the size of the cassette. By means of adjustment of the potentiometers 37a, 37b 37c, the desired beam limitation imposed by the diaphragm 2 can be automatically controlled through the closing of one of the relay contacts 37a, b, or c in the manner discussed in connection with FIG. 5 which, however shows a two relay system. The same circuit arrangement can also be provided for the second pair of laminaes within the diaphragm 2.

Figure 7:
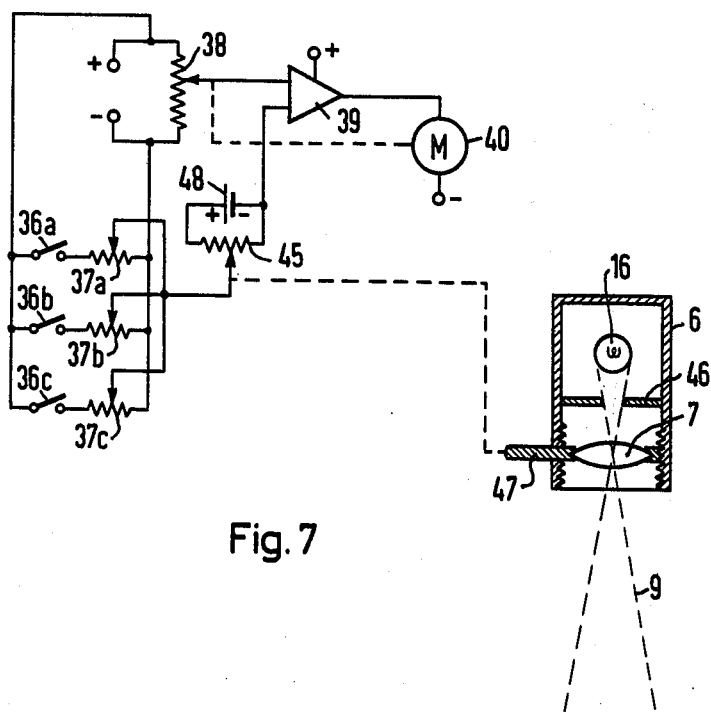
FIG. 7 is a control circuit providing a further computing circuit for adjusting the diaphragm.

Additionally, in order to properly set the light beam 9 with respect to the different cassette sizes an adjusting device 47 which focuses the light beam is provided and is illustrated in FIG. 7. Again, this focusing device, is designed to provide for a desired signal generation when the particular focus to film distance for which the focusing system is adjusted exists. This signal can be combined with the signal explained in FIGS. 5 and 6 and may be fed to a computation circuit for controlling the motors 40 to properly set the diaphragm 2 such that the X-ray beam will be properly limited so that its margins lie within the plane of the film cassette 4 and coincide with the edges 18 of the film cassette even when different focused film distances are used. Light source 16 is associated with a slit diaphragm 46 and a lense system in a housing for the purpose of both limiting the outlines of and properly focusing the beam 9. The lens system is attached, for example, to a rotatable lever which causes the lens to move longitudinally of the housing towards and away from the light source 16 therey properly focusing the light beam for the particular focus to film distance being used.

The required signal, dependent upon the focus to film distance, is determined as the voltage from potentiometer 45 which is connected to a voltage source 48. The potentiometer is mechanically connected with the lever 47 of the focusing system 6, 7, 47. If the output voltage of the potentiometer 45 is proportional to the logarithm of the focus to film distance, and if the output voltage of the potentiometers 37a, 37b and 37c are proportional to the logarithm of the cassette edge length, the difference between these series connected voltages is a linear function of the logarithm of the aperture distance or of the separation between the laminae 3 in the main diaphragm. Once again, the second pair of diaphragm plates within the main diaphragm 2 can be associated with a similar or the same circuit arranged in connection with the second motor.

It can therefor be seen from the above that this invention provides an X-ray unit where there is no mechanical linkage between the X-ray source and the film and where both are independently movable in random directions with respect to one another. The invention provides a means for simply, accurately, and expeditiously assuring alignment of the X-ray beam with the cassette both at right angles to the plane of the cassette and limited to the boundaries of the film. In addition the device has automatic systems for use with a variety of cassette sizes and accommodating different focus-to-film distances. The device incorporates a light source rigidly fixed to the X-ray tube which is permeable onto an extension of the cassette to illuminate a previously defined marked area to allow for visual indication of a proper setting of the cassette with respect to the X-ray tube. Various modifications shown teach the use of this overall light beam concept in connection with automatic circuitry to provide automatic focusing of the X-ray beam.

Although the teachings of my invention have herein been discussed with reference to specific theories and embodiments, it is to be understood that these are by way of illustration only and that others may wish to utilize my invention in different designs or applications.

I claim as my invention:

1. In an X-ray photographic apparatus having an X-ray tube a primary diaphragm which defines the X-ray beam from the tube, the tube being mounted in a manner which allows the beam to be directed as desired, a film cassette which is independently movable with respect to the X-ray beam, the improvement of a light source fixedly positioned with respect to the primary diaphragm and/or the X-ray tube, the light source provided with focusing means for sharply defining a light beam emitted from the light source, a designated area light receiving device on an assembly including the cassette, said light receiving device having recognition characteristics indicating, as a function of the alignment of the impinging light beam from the light source on the light receiving device whether the position of the cassette film edges is in dependent relationship to the edges of the X-ray beam field and whether the central ray of the X-ray beam is perpendicular to the center of the cassette film, the light source and light receiving device positioned with respect to the primary diaphragm and the cassette such that the light beam from the light source is not blocked by a patient positioned over the film in the cassette.

2. The device of claim 1 further including means associated with the light receiving device and the light source beam indicating whether a desired focus-to-film distance exists between the cassette film and the X-ray beam focus.

3. The device of claim 2 wherein the light receiving device includes a defined area field fixedly associated with said cassette, the determination of the position of the cassette film edges in relation to the edges of the X-ray beam field being in dependent relationship to the alignment of the light source beam with the defind area field, the light receiving device further including a means for determining whether the light beam from the light source is aligned substantially perpendicularly to the plane of the cassette.

4. The device according to claim 3 wherein the means for determining comprises a shadow producing device mounted in fixed relationship to the cassette.

5. The device of claim 3 wherein the field is a marking on a member fixedly attached to the cassette.

6. The device according to claim 3 wherein the primary diaphragm limits the X-ray beam to a quadralateral cross-section field and wherein the light beam from the light source is sharply defined producing a light beam having a defined cross-sectional geometric shape, and the defined area field of the device receiving the light beam has edge defining means alignable with edges of the light beam whereby alignment of the light beam with the edges of the defined area indicates that the edges of the radiation beam are aligned in parallelism with the edges of the cassette film.

7. The device according to claim 6 wherein the defined field receiving the light source is a rectangular field and wherein the light beam from the light source has a rectangular cross-section.

8. The device according to claim 4 wherein the shadow producing device includes a member projecting from a surface of the cassette assembly which throws a shadow on a portion of the surface of the cassette assembly, the portion of the surface of the cassette assembly being marked defining with a field alignable with the shadow.

9. The device according to claim 4 wherein the field alignable with the shadow coincides with the defined area field.

10. The device according to claim 6 wherein recognition characteristic indicating a perpendicular beam is a cassette assembly carried device which includes a hollow axially elongated member projecting from the cassette assembly having axial walls which are light impenetrable, a light sensing device positioned at a bottom of an axially hollow portion, the light sensing device producing a first signal when the light beam penetrates the axial length of the hollow portion and impinges upon the light sensing device, said first signal coupled to a circuit blocking actuation of the X-ray tube in the absence of said first signal.

11. A device according to claim 10 wherein a second light sensing device is associated with the defined area field, said second light sensing device providing a second signal indicating alignment of the edges of the light source impinging upon the defined area field with edges of the defined area field, said second signal providing input to a circuit which blocks actuation of the X-ray tube in the absence of the signal.

12. A device according to claim 11 wherein a plurality of cassette assemblies of different physical dimension are utilizable in the device, each of said different cassette assemblies being equipped with means for generating a third signal which is specific to the physical dimension of that cassette.

13. A device according to claim 12 wherein circuitry is provided which, in response to receipt of one of the third signals specific to a physical dimension of a cassette controls servomechanisms to adjust the primary diaphragm to limit the X-ray beam in such a manner that its edges will coincide with the edges of the portion of the film cassette to be exposed to the X-ray beam when the presence of the first and second signals indicates that the beam is aligned at right angles to the surface of the cassette film and that the beam edges are aligned with the edges of the cassette film.

14. A device according to claim 13 including a focusing assembly for the light source which is adjustable to allow limitation of the light beam to a defined area for different focus-to-film distances.

15. A device according to claim 14 wherein the focusing system provides a fourth signal dependent upon the particular focus-to-film distance for which the focusing system has been adjusted, said fourth signal and the third signal being supplied to a computational circuit, said computational circuit actuating servomechanism to control the setting of the primary diaphragm whereby the X-ray beam is limited to different degrees for different focus-to-film distances to have boundaries coinciding with the boundaries of the film to be exposed in the cassette.

16. An X-ray photographic apparatus having an X-ray tube with an associated diaphragm mounted on a support for random movement, a light source rigidly affixed in fixed position relative to a beam eminating from said diaphragm, a cassette assembly including a film holding section and a projection, said projection having a marked field thereon of defined area, a focusing system for said light source for projecting a light beam having a predetermined cross-sectional configuration, said light beam directable at said cassette projection and being able to illuminate said marked field, the edges of the defined light beam being alignable with edges of the marked field such that when aligned, edges of the X-ray beam from the primary diaphragm will be aligned with edges of the film in the film cassette means on said projection indicating when the light beam from said light source is perpendicular to the film cassette, said light beam being parallel to a central ray of said X-ray beam.

17. The device of claim 16 wherein the means indicating that the light beam is perpendicular to the film cassette includes a member projecting from a surface of the projection to said film cassette, the member being partially impenetrable to said light at a point spaced from the surface of the cassette projection whereby portions of said light beam passing said light absorptive portions of said projection and impinging upon the projection of the film cassette indicate whether the light beam is perpendicular to the plane of the film cassette.

18. A device according to claim 17 including a circuit means for generating first, second and third signals, said first signal generated by alignment of said light beam with said marked field defined area, said second signal generated by said means for indicating that the light beam is perpendicular to the plane of the film cassette, and said third signal generated in dependent relationship to the geometric configuration of the film cassette, said first, second and third signals providing imput to a computational blocking circuit said computational circuit controlling actuation of servomechanisms adjusting setting of the primary diaphragm, and said blocking circuits blocking actuation of the X-ray tube in absence of the first and second signals.

19. A device according to claim 18 including adjustable focusing means for said light source allowing adjustment of said light source for different focus-to-film distances, adjustment of said light source affecting said computational circuit for controlling said servo-motors whereby adjustment of the primary diaphragm is automatically changed for different focus-to-film distances.

* * * * *